(12) United States Patent
Hernandez et al.

(10) Patent No.: US 8,813,749 B2
(45) Date of Patent: Aug. 26, 2014

(54) CUSHION FOR VENTILATION INTERFACE

(75) Inventors: Shara Hernandez, Davie, FL (US);
Louis Javier Collazo, Pompano Beach, FL (US)

(73) Assignee: Mergenet Solutions, Inc., Coconut Creek, FL (US)

( * ) Notice: Subject to any disclaimer, the term of this patent is extended or adjusted under 35 U.S.C. 154(b) by 0 days.

(21) Appl. No.: 13/494,518

(22) Filed: Jun. 12, 2012

(65) Prior Publication Data

US 2012/0247475 A1    Oct. 4, 2012

Related U.S. Application Data

(63) Continuation of application No. 12/266,707, filed on Nov. 7, 2008, now Pat. No. 8,215,305.

(60) Provisional application No. 60/996,229, filed on Nov. 7, 2007.

(51) Int. Cl.
*A62B 18/08* (2006.01)
*A62B 18/10* (2006.01)
*A61M 16/06* (2006.01)

(52) U.S. Cl.
CPC ........... *A61M 16/06* (2013.01); *A61M 16/0616* (2014.02); *A61M 16/0622* (2014.02); *A61M 16/0633* (2014.02)
USPC ................................. 128/206.24; 128/206.12

(58) Field of Classification Search
USPC .................................................. 128/200–207
See application file for complete search history.

(56) References Cited

U.S. PATENT DOCUMENTS

| | | | |
|---|---|---|---|
| 5,492,116 A | 2/1996 | Scarberry et al. |
| 5,655,527 A | 8/1997 | Scarberry et al. |
| 6,634,358 B2 | 10/2003 | Kwok et al. |
| 6,772,760 B2 | 8/2004 | Frater et al. |
| 6,823,869 B2 | 11/2004 | Raje et al. |
| 6,986,352 B2 | 1/2006 | Frater et al. |
| 7,007,696 B2 | 3/2006 | Palkon et al. |
| 7,107,989 B2 | 9/2006 | Frater et al. |
| 7,178,527 B2 | 2/2007 | Kwok et al. |
| 7,207,335 B2 | 4/2007 | Kwok et al. |
| 7,287,528 B2 | 10/2007 | Ho et al. |
| 7,318,439 B2 | 1/2008 | Raje et al. |
| 7,631,644 B2 | 12/2009 | Ho et al. |
| 7,845,354 B2 | 12/2010 | Kwok et al. |
| 2001/0020474 A1 | 9/2001 | Hecker et al. |
| 2004/0118406 A1 | 6/2004 | Lithgow et al. |
| 2006/0118117 A1 | 6/2006 | Berthon-Jones et al. |
| 2006/0201515 A1 | 9/2006 | Kwok et al. |
| 2006/0213520 A1 | 9/2006 | Frater et al. |
| 2008/0178885 A1 | 7/2008 | Raje et al. |
| 2009/0095303 A1 | 4/2009 | Sher et al. |
| 2009/0107506 A1 | 4/2009 | Collazo et al. |
| 2009/0114230 A1 | 5/2009 | Hernandez et al. |
| 2010/0000543 A1 | 1/2010 | Berthon-Jones et al. |
| 2010/0065060 A1 | 3/2010 | Ho et al. |
| 2010/0199992 A1 | 8/2010 | Ho et al. |

OTHER PUBLICATIONS

International Search Report dated Jun. 17, 2009 in corresponding International Patent Application No. PCT/US08/82760—3 pages.

*Primary Examiner* — Stephen Crow
(74) *Attorney, Agent, or Firm* — Maier & Maier, PLLC

(57) ABSTRACT

In accordance with at least one exemplary embodiment, a cushion for a ventilation interface is disclosed. A ventilation mask can include a mask body adapted to matingly engage with the cushion. The cushion can be a double-membrane cushion having an outer sealing membrane and an inner membrane, both of which can extend from a frame. The outer sealing membrane can have a face-contacting portion. The inner membrane can be outwardly oriented from the frame.

17 Claims, 8 Drawing Sheets

CUSHION FOR VENTILATION INTERFACE

RELATED APPLICATIONS

This application is a continuation of U.S. patent application Ser. No. 12/266,707, filed Nov. 7, 2008, which claims priority under 35 U.S.C. §119(e), to U.S. Provisional Patent Application No. 60/996,229, filed Nov. 7, 2007, the disclosures of which are incorporated by reference herein in their entireties.

BACKGROUND

Ventilation interfaces requiring a cushion for providing a seal with a user's face are used for various applications. One such application involves current treatments for obstructive sleep apnea syndrome.

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit an adequate amount of oxygen to flow into the lungs. However, in those individuals having a relatively smaller-sized throat passage, the narrowed throat passage prohibits an adequate amount of oxygen from flowing into the lungs. Additionally, a nasal obstruction, such as a relatively large tongue, and/or certain shapes of the palate and/or the jaw of the individual, further prohibit an adequate amount of oxygen from flowing into the lungs.

An individual having the above-discussed conditions can stop breathing for one or more prolonged periods of time (e.g., ten seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and depression.

Other medical conditions can also prevent individuals, including adults and infants, from receiving an adequate amount of oxygen into the lungs. For example, an infant who is born prematurely can have lungs that are not developed to an extent necessary to receive an adequate amount of oxygen. Further, prior to, during and/or subsequent to certain medical procedures and/or medical treatments, an individual can be unable to receive an adequate amount of oxygen.

Under these circumstances, it is known to use a ventilation interface to apply a positive pressure to the throat of the individual, thereby permitting an adequate amount of oxygen to flow into the lungs. In known ventilation interfaces, oxygen and/or room air containing oxygen is delivered through the mouth and/or nose of the individual.

Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV) in which a positive pressure is applied when apnea is sensed (I.e., the positive airway pressure is applied intermittently or non-continuously)

Ventilation interfaces of ventilation systems include nasal masks and full masks, among others. For example, many nasal ventilation systems include a mask interface that fits over the nose of a user. The mask is intended to provide a space of gas (e.g., air) for inhalation into the lungs for respiration. Such systems frequently suffer from gas leakage, creating an inability to assure ventilation in many users.

For example, some conventional masks incorporate a sealing surface that extends around the periphery of the mask. The sealing surface is often a molded or formed surface made from a resilient material including elastomers such as plastics, rubbers and foams. Such masks have performed well when the fit is good between the contoured sealing surface and the corresponding contours of the user's face.

Nevertheless, some users will not have an optimal seal fit and gaps in the seal-to-face interface do occur. Often this is remedied by applying greater force to further compress the sealing surface against a user's face, thereby attaining a seal in those areas where the gaps occurred. This often produces user discomfort and may produce various types of skin irritation, particularly where the applied force exceeds the local perfusion pressure (i.e. the pressure that is sufficient to cut off surface blood flow).

Also, because many conventional ventilation systems use a headgear system having straps to bind the mask in place; the system is tightened to obtain a sufficient seal if one does not exist. The mask, headgear and/or individual straps thereby place greater pressure on the patient's face and/or head. Thus, discomfort to a patient can occur at places remote from the sealing surface.

Sealing problems causing discomfort are often exacerbated when the positive pressure of the gas being supplied is relatively high or is cyclical to high levels. The mask must be held against the face with a force sufficient to seal against leakage of the peak pressure of the supplied gas and as the gas pressure increases so does the needed force to prevent leakage.

Overall, user discomfort must be taken into consideration as it may well cause discontinued cooperation with the treatment regimen.

Various cushions for ventilation mask are known. For example, numerous patents teach nasal cushions for nasal masks, such as related U.S. Pat. No. 6,112,746 (Kwok et al.), U.S. Pat. No. 6,357,441 (Kwok et al.) and U.S. Pat. No. 6,634,358 (Kwok et al.), assigned to ResMed, Inc., the disclosures of which are hereby incorporated by reference in their entireties.

SUMMARY

According to at least one embodiment, a ventilation mask can include a mask body adapted to matingly engage with a cushion. The cushion can be a double-membrane cushion having an outer sealing membrane and an inner membrane, both of which can extend from a frame. The outer sealing membrane can have a face-contacting portion. The inner membrane can be outwardly oriented from the frame.

In another exemplary embodiment, a double-membrane nasal cushion for a nasal mask can include a frame. Extending from portions of the frame can be an outer sealing membrane and an inner membrane. The outer sealing membrane can have a face-contacting portion. The inner membrane can be outwardly curved.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the terms "embodiments of the invention", "embodiment" or "invention" do not require that all embodiments of the invention include the discussed feature, advantage or mode of operation.

Cushion embodiments can be designed to cooperate with nearly any ventilation interface that makes use of a cushion for sealing engagement with portions of a user's face. For examples, embodiments can be designed to cooperate with nasal masks, oral masks, full masks and portions of hybrid masks (i.e. those masks having an oral cavity and either nasal inserts or nasal prongs) of various styles and shapes as will be appreciated by those having ordinary skill in the art.

Nevertheless, for illustrative purpose and in a non-limiting fashion, at least one exemplary embodiment is described herein in reference to nasal masks, particularly nasal masks having a generally triangular portion adapted to mate (with or without additional mounting components) with a nasal cushion having a substantially triangularly-shaped (i.e. three-sided) frame. The nasal cushion can be a double-membrane cushion having an outwardly oriented inner membrane.

Figure 1:
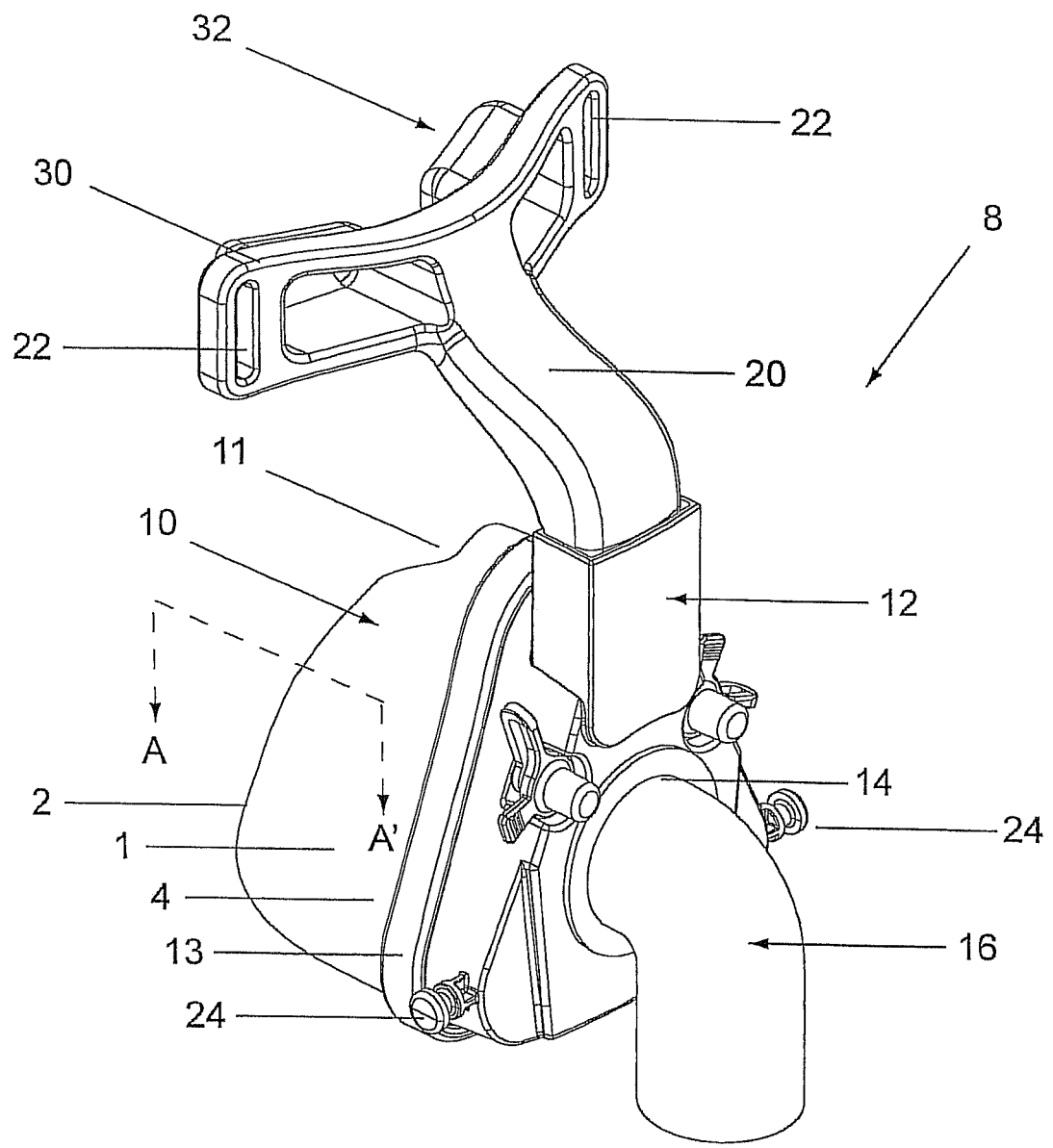
FIG. 1 is a side perspective view of an exemplary nasal mask.
Figure 5:
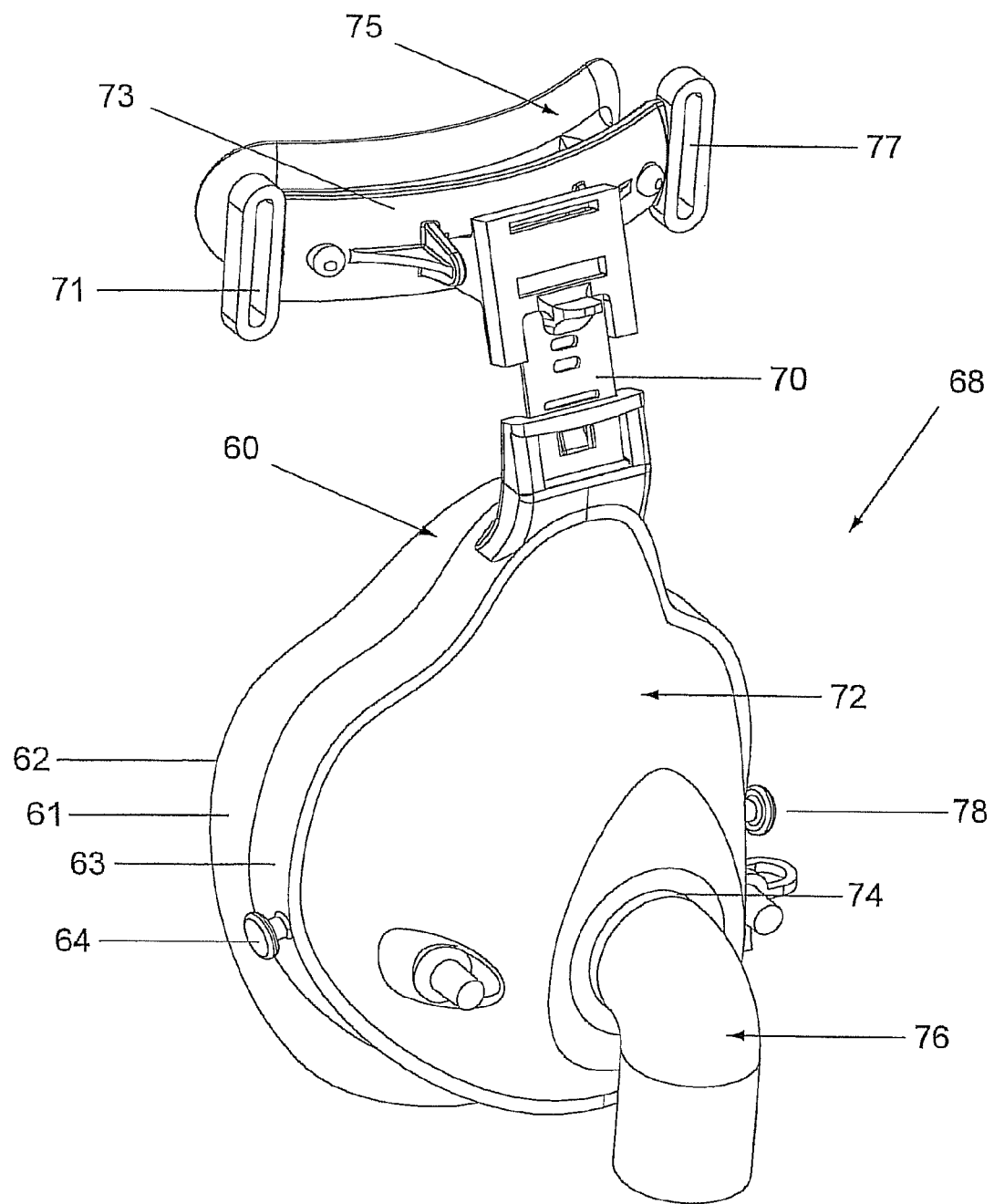
FIG. 5 is a side perspective view of an exemplary full mask.
Figure 6:
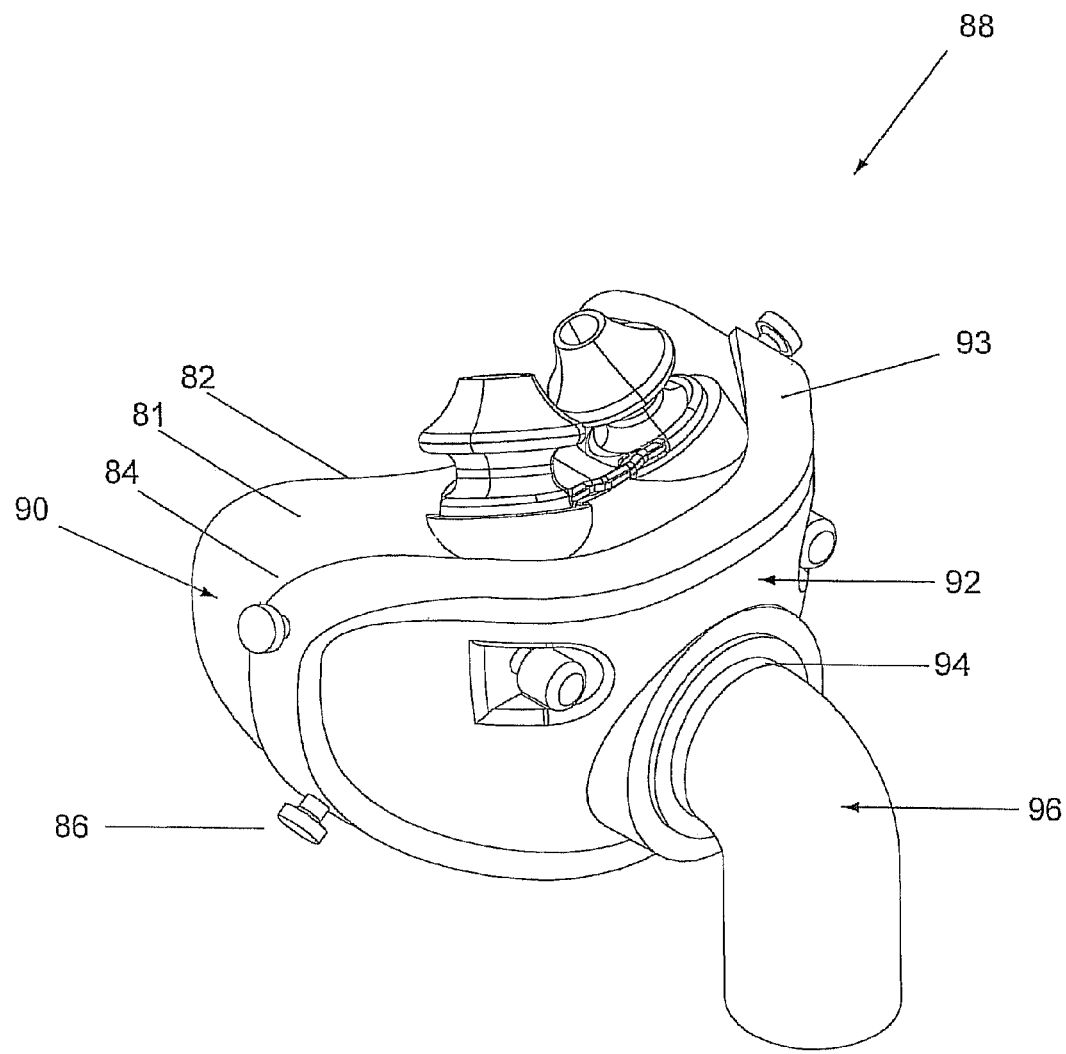
FIG. 6 is a side perspective view of an exemplary hybrid mask.

Referring to FIGS. 1, 5 and 6, nasal ventilation mask 8, 68 and 88 for use with a ventilation device (e.g., CPAP units, BiPAP units and IPPV units) is shown. Mask 8, 68 or 88 can include cushion 10, 60 and 90 mated to mask shell 12, 72 or 92 through coupling of cushion mating edge 4, 61 or 84 and mask mating edge 13, 63, or 93 defined respectively thereon. For instance, mating edge 4, 61 or 84 can be defined on substantially triangularly-shaped frame 1, 61 or 81 of cushion 10, 60 or 90. Correspondingly, mating edge 13, 63 or 93 can be a generally triangular portion of mask shell 12, 72 or 92, which can be generally perimetrical in nature as related to mask shell 12.

As one non-limiting example, mating edge 4, 61 or 84 and mating edge 13, 63 or 93 can be either the female edge or the male edge of a tongue-and-groove attachment system. For example, mating edge 4, 61 or 84 can be formed to include a grooved edge adapted to received a tongue (ridge) formed on mating edge 13, 63 or 93. Additional mounting components, such as a mounting ring (not shown), can be provided to more securely hold mating edge 4, 61 or 84 and mating edge 13, 63 or 93 in mating engagement. Alternatively, a barb (not shown) can be formed in the grooved edge of mating edge 4, 61 or 84 to provide a more secure engagement. Regardless of the exact mating engagement, cushion 10, 60 or 90 can be removably engaged with mask shell 12, 72 or 92 to allow for replacement.

Alternatively, cushion 10, 60 or 90 can be permanently attached to mask shell 12, 72 or 92 by any means known to one having ordinary skill in the art. For example, cushion 10, 60 or 90 can be glued to mask shell 12, 72 or 92 or cushion 10, 60 or 90 can be integrally formed with mask shell 12, 72 or 92 by any conventional molding process known to one having ordinary skill in the art.

Figure 7:
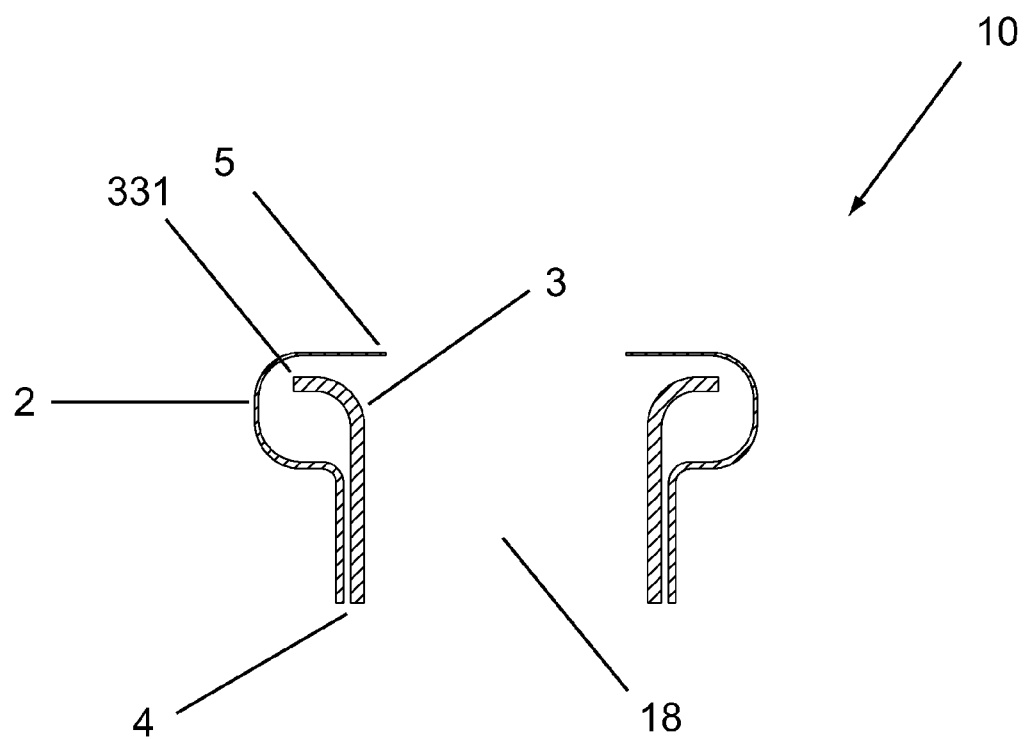
FIG. 7 is a cross-sectional view of a further exemplary cushion taken along line AA' of FIG. 1.

With respect to FIGS. 1-6 cushion 10, 40, 50, 60 or 90 can be a double-membrane cushion. having outer sealing membrane 2, 42, 52, 62 or 82 and inner membrane 3, 43 or 53. Outer sealing membrane 2, 42, 52, 62 or 82 and inner membrane 3, 43 or 53 can both extend from frame 1, 41, 51, 61 or 81. Alternatively, outer sealing membrane 2, 42, 52, 62 or 82 and inner membrane 3, 43 or 53 can be separate for example as shown in FIG. 7. Either or both of outer sealing membrane 2, 42, 52, 62 or 82 and inner membrane 3, 43 or 53 can assemble directly to mask shell 12, 72 or 92 or assemble directly to frame 1, 41, 51, 61 or 81 or any combination thereof. For example, inner membrane 3, 43 or 53 may extend integrally from frame 1, 41, 51, 61 or 81 and outer sealing membrane 2, 42, 52, 62 or 82 may be attached to mask shell 12, 72 or 92 or outer sealing membrane 2, 42, 52, 62 or 82 may be non-integrally attached to any portion of cushion 10, 40, 50, 60 or 90. Further, in at least one exemplary embodiment, more than two membranes can be present.

Outer sealing membrane 2, 42, 52, 62 or 82 can be thinner and more flexible than inner membrane 3, 43 or 53. A portion of sealing membrane 2, 42, 52, 62 or 82 can be a sealing portion that can be held against portions of a user's face when in use. For example, the sealing portion of sealing membrane 2, 42, 52, 62 or 82 can make contact with a user's face, when in use, proximate the bridge of the nose, around the cheeks, and proximate the skin between the upper lip and the base of the nose. Cushion 10 can have indentation 11 formed in a contoured fashion to receive the bridge of a user's nose.

Figure 8:
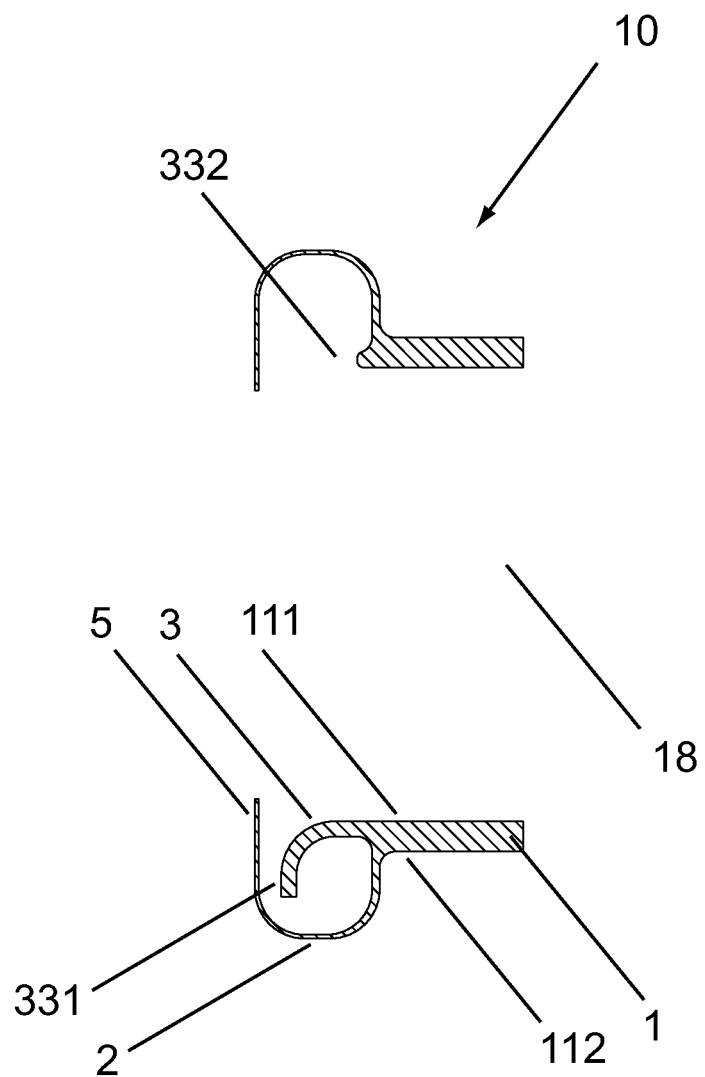
FIG. 8 is an exemplary cross-sectional view through a nasal bridge region of a cushion.

In at least one exemplary embodiment, inner membrane 3, 43 or 53 can have notched and cut-out (missing) portions. For example, the nasal bridge region of inner membrane 3 can be removed (cut-out) for example as demonstrated by notch 332 in FIG. 8, which is a cross-sectional view through the nasal bridge region of the cushion 10 and 60. Such design features are not to be considered outside the scope of an inner membrane in accordance with at least one embodiment. As described further below, inner membrane 3, 43 or 53 can be outwardly oriented.

Mask shell 12, 72 or 92 can also include port 14, 74 or 94. Coupling tube 16, 76 or 96 can be provided in fluid communication with mask 8, 68 or 88 via port 14, 74 or 94. Coupling tube 16, 76 or 96 can be swivelably attached to mask shell 12, 72 or 92. Coupling tube 16, 76 or 96 can be fitted with additional tubing (not shown) leading to a ventilation device (not shown) to provide, for example, gas under positive pressure to a user. Gas can be provided under pressure to central passageway 18, 48 or 58 formed within the cavity defined by cushion 10, 40, 50, 60 or 90. Central passageway 18, 48, or 58 can also function as a nose-receiving cavity when in use.

Arm 20 or 70 can extend from mask shell 12 or 72. The arm 20 or 70 can be assembled to the mask shell 12 or 72 or could be integral with the mask shell. Arm 20 or 70 may have a pad (not shown) disposed to provide a comfortable association between the arm and the user's forehead. Alternatively, arm 20 or 70 may also have a cross bar 30 or 73, with at least one pad 32 or 75. The pad 32 or 75 can also be made of a unitary piece of flexible material, for example silicone elastomer, foam, gel, and other like materials. The arm 20 or 70, crossbar 30 or 73, and pad 32 or 75 can be made of the same materials or different materials. For example, the arm 20 or 70 can be made of rigid plastic, the cross bar 30 or 73 can be made of silicone, and the pad 32 or 75 can be a gel or foam material. It is contemplated that these components can be made of any of the group of materials that includes silicon, rigid plastic, gel, foam and the like as known to one of skill in the art. Two slots (not shown) can be defined proximate the arm 20 or 70 for receiving headgear upper fastening straps. Alternatively, slots 22 or 71 can be defined on terminating ends of cross bar 30 or 70 for receiving upper headgear fastening straps (not shown). Mask shell 12, 72 or 92 can include connection points 24, 64 or 86 or slots for receiving lower headgear fastening straps (not shown) or quick-release buckles (not shown). The number and location of headgear connection points and slots can vary according to desired comfort or stability.

Mask shell 12, 72 or 92, coupling tube 16, 76 or 96, arm 20 or 70 and connection points 24, 64 or 86 can all be formed of a plastic, for example, by conventional molding processes, as is known to one having ordinary skill in the art. In at least one exemplary embodiment, mask shell 12, 72 or 92, arm 20 or 70 and connection points 24, 64 or 86 can be formed integrally by conventional molding processes, as is known to one having ordinary skill in the art. Alternatively, arm 20 or 70 can be two or more pieces for providing an adjustable arm, as is also known to one having ordinary skill in the art.

The components of cushion 10, 40, 50, 60 or 90 can be formed integrally by conventional molding processes. Cushion 10, 40, 50, 60 or 90 can be more flexible than mask shell 12, 72 or 92. Cushion 10, 40, 50, 60 or 90 can also be resilient. For example, cushion 10, 40, 50, 60 or 90 (and the components thereof) can be formed from an elastomeric material, such as a silicone elastomer. Moreover, inner membrane 3, 43 or 53 can be made of various flexible materials, such as silicone elastomers, gels, foams and the like known to one having ordinary skill in the art.

Outer sealing membrane 2, 42, 52, 62 or 82 and inner membrane 3, 43 or 53 can be substantially triangularly-shaped in whole; similar to frame 1 or 61 from which they can both extend. Nevertheless, outer sealing membrane 2, 42, 52, 62 or 82 and inner membrane 3, 43 or 53 may have notches and cut-out regions. A membrane can have cut-outs in one or more regions and may still be deemed substantially triangularly-shaped even if the three-side shape is incomplete.

Figure 2:
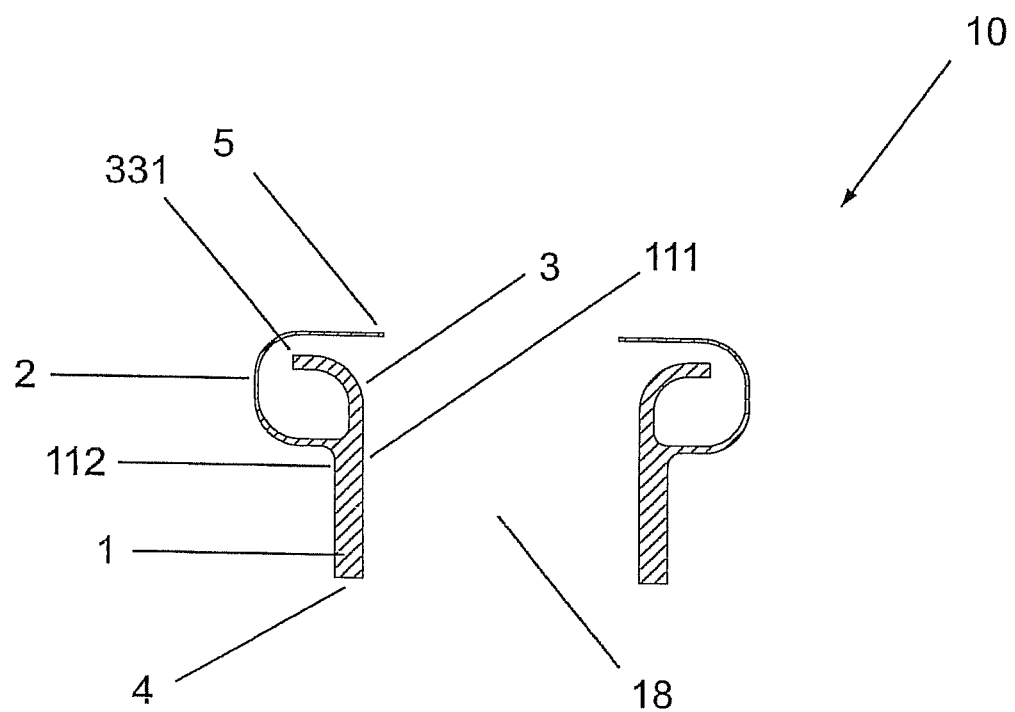
FIG. 2 is a cross-sectional view of an exemplary cushion taken along line AA' of FIG. 1.
Figure 3:
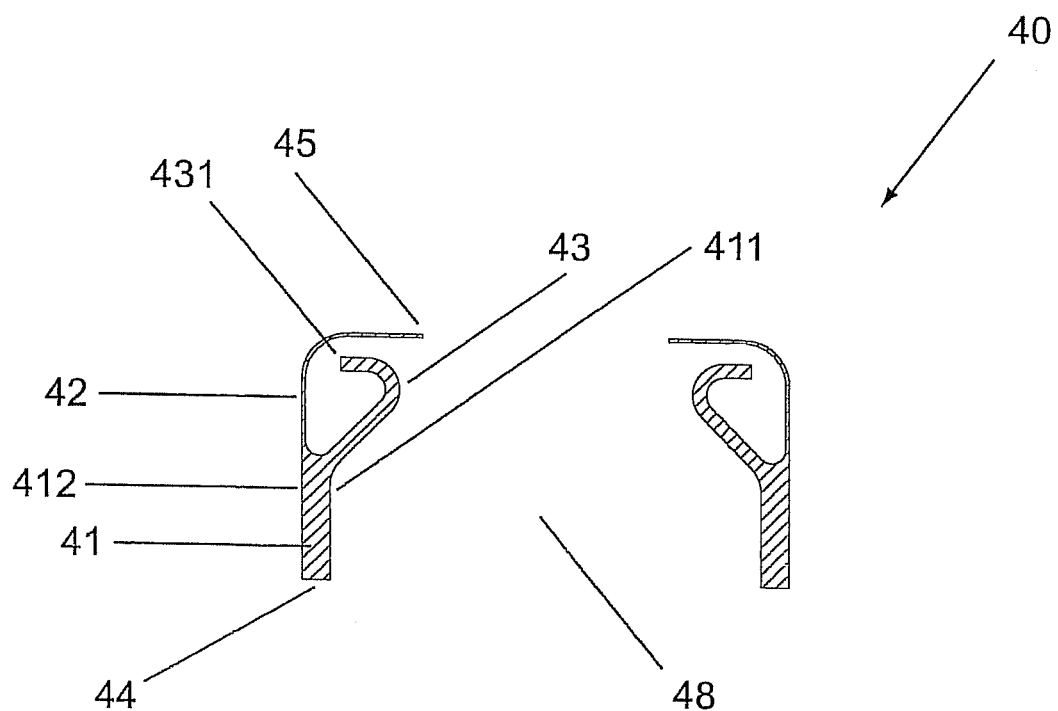
FIG. 3 is a cross-sectional view of another exemplary cushion taken along line AA' of FIG. 1.
Figure 4:
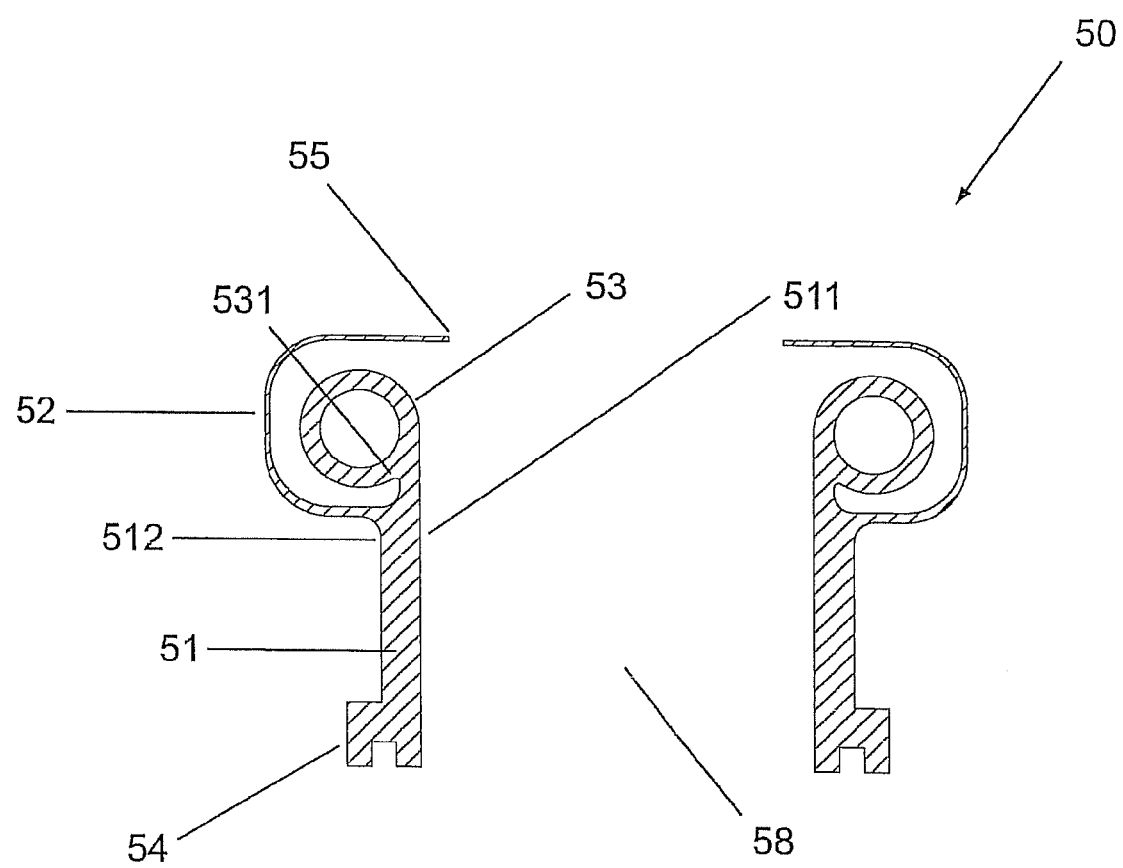
FIG. 4 is a cross-sectional view of a further exemplary cushion taken along line AA' of FIG. 1.

Now referring to FIGS. 2-4, where a cross-sectional view of a portion of double-membrane cushion 10, 40 and 50 is shown. Outer sealing membrane 2, 42 and 52 and inner membrane 3, 43 and 53 can extend from a first side of the wall of frame 1, 41 or 51. Outer sealing membrane 2, 42 or 52 can be thinner and thus more flexible than inner membrane 3, 43 or 53. In at least one exemplary embodiment where the cushion is formed from an elastomer such as silicone, outer sealing membrane 2, 42 or 52 can have a thickness of between about 0.20 mm and 0.50 mm. Inner membrane 3, 43 or 53 can have a thickness of between about 1.0 mm and 2.0 mm. Frame 1, 41 or 51 can be about as thick or can have a greater thickness than the combined thicknesses of outer membrane 2, 42 or 52 and inner membrane 3, 43 or 53 at the thickest point of frame 1, 41 or 51.

The second side (cushion mating edge) 4, 44 or 54 of the wall of frame 1, 41 or 51 can be directed towards mating geometry with mask shell 12, 72 or 92. For example, cushion mating edge 4, 44 or 54 can have a groove (not shown) defined substantially in the middle thereof adapted to receive a ridge (not shown) formed on mask mating edge 13, 63 or 93.

Outer sealing membrane 2, 42 or 52 can be inwardly oriented. For example, outer sealing membrane 2, 42 or 52 can extend from frame 1, 41 or 51 and be curved inwardly where outer membrane edge 5, 45 or 55 generally defines an opening to central passageway 18, 48 or 58 within mask 8, 68 or 88 for receiving a user's nose and/or mouth. Outer membrane edge 5, 45, or 55 is located at the terminating end of outer sealing membrane 2, 42, and 52. Alternatively, outer sealing membrane 2, 42 or 52 can be inwardly oriented without curvature (not shown) and may be formed in various shapes. For example, outer sealing membrane 2, 42 or 52 can be angular in construction (not shown). The portion of the outer sealing membrane 2, 42, or 52 where it immediately extends from frame 1, 41, or 51 is known as the lower portion of the outer sealing membrane.

Outer membrane edge 5, 45 or 55 can be adjacent a user's nose or mouth and may contact portions of a user's nose or mouth. In at least one exemplary embodiment, outer sealing membrane 2, 42 or 52 can have a sealing portion for contacting portions of a user's nose that can generally run from (or be within) edge 5, 45 or 55 up to portions of outer membrane 2, 42 or 52 that overlap the outwardly oriented portion of inner membrane 3, 43 or 53. The remainder (non-sealing portions) of sealing membrane 2, 42 or 52 can face the atmosphere outside of cushion 10, 40 or 50.

Inner membrane 3, 43 or 53 can be outwardly oriented as compared to outer sealing membrane 2, 42 or 52, which can be inwardly oriented. Inner membrane 3, 43 or 53 can extend from frame 1, 41 or 51 and can be curved outwardly until inner membrane edge 331, 431, or 531. Inner membrane edge 331, 431, or 531 is located at the terminating end of inner membrane 3, 43, or 53. Alternatively, inner membrane 3, 43 or 53 can be outwardly oriented without curvature (not shown) and may be formed in various shapes. For example, inner membrane 3, 43 or 53 can be angular in construction (not shown). The portion of the inner membrane 3, 43, or 53 where it immediately extends from frame 1, 41, or 51 is known as the lower portion of the inner membrane. Likewise, the portion of frame 1, 41, or 51 where inner membrane 3, 43, or 53 immediately extends from is known as the upper portion of the frame. This upper portion of the frame 1, 41, or 51 can have an inner frame surface 111, 411, or 511 and an outer frame surface 112, 412, or 512.

An outwardly oriented membrane forming inner membrane 3, 43 or 53 may provide one or more benefits over conventional double-membrane cushions as will be appreciated by one having ordinary skill in the art. Particularly, an outwardly oriented inner membrane 3, 43 or 53 may provide increased support and comfort as compared to at least some conventional double-membrane cushion known to those having ordinary skill in the art.

Outer sealing membrane 2, 42 or 52 and inner membrane 3, 43 or 53 can be spaced (variably or constantly) from each other in each cross-section, as well as between cross-sections of cushion 10, 40 or 50. Particularly, the inner surface of outer sealing membrane 2, 42 or 52 and the outer surface of inner membrane 3, 43 or 53 can be facing each other and can be spaced. Since, in at least one exemplary embodiment, portions of inner membrane 3, 43 or 53 may be notched or cut-out, inner membrane 3, 43 or 53 would appear abridged (e.g., missing the outwardly curved portion) or wholly missing, respectively, in cross-section at such portions. Moreover, outer sealing membrane 2, 42 or 52 and inner membrane 3, 43 or 53 can be contoured in a variety of ways. For example, outer sealing membrane 2, 42 or 52 and inner membrane 3 can be differently contoured so as to be variable spaced when comparing cross-sections taken from different portions of cushion 10, 40 or 50. Further, contouring of, for instance, outer sealing membrane 2, 42 or 52 may create differing lengths for outer sealing membrane 2, 42 or 52 as measured from the extension point at the intersection of membrane 2, 42 or 52 and frame 1, 41 or 51 to edge 5, 45 or 55. Thus, edge 5, 45 or 55 can be positioned further and, conversely, retracted when comparing cross-sections taken from different portions of cushion 10, 40 or 50.

When properly fitted on a user, a user's nose can be received in breathing chamber 18, 48 or 58 where the majority of a user's nose or mouth may enter past outer membrane edge 5, 45 or 55 defining the entry aperture of breathing chamber 18, 48 or 58. Portions (i.e., the sealing portion) of outer sealing membrane 2, 42 or 52 can contact areas proximate a user's nose, including proximate the bridge of the nose, around the cheeks, and proximate the skin between the upper lip and the base of the nose.

Depending on the tension applied to fastening straps of a headgear, it can be expected that outer sealing membrane 2, 42 or 52 and inner membrane 3, 43 or 53 will remained spaced while an effective seal can still be provided proximate the nose of a user. The seal may not be dependent on the provision of positive pressurized gas to breathing chamber 18, 48 or 58. Nevertheless, pressurized gas may aid in strengthening or maintaining the seal formed by outer sealing membrane 2, 42 or 52.

If nasal mask 8, 68 or 88 is pressed sufficiently tight to a user's face proximate the user's nose, such as by tensioning of fastening straps, outer sealing membrane 2, 42 or 52 can be expected to deform into contact with inner membrane 3, 43 or 53. Inner membrane 3, 43 or 53 can thus act as a stopper to hinder further deformation of outer sealing membrane 2, 42 or 52. Particularly, the opposing orientations of outer sealing membrane 2, 42 or 52 and outwardly oriented inner membrane 3, 43 or 53 can aid in providing stopper functionality while maintaining comfort. Without being bound by theory, outwardly oriented inner membrane 3, 43 or 53 can trap gas forming a gas pocket that may prop inner membrane 3, 43 or 53, which may assist in providing stopper functionality.

Also, without being bound by theory, the outward orientation of inner membrane 3, 43 or 53 can provide stopper functionality without unnecessarily interfering with portions of outer sealing membrane 2, 42 or 52 proximate edge 5, 45 or 55. Such decreased interference may provide greater freedom of movement to outer sealing membrane 2, 42 or 52 that may maintain a space between outer membrane 2, 42 or 52 and inner membrane 3, 43 or 53 under somewhat increased tensioning force at least at certain portions of cushion 10, 40 or 50. Comfort may be maintained due to spacing between outer membrane 2, 42 or 52 and inner membrane 3, 43 or 53 even if nasal mask 8 is pressed more tightly than what may otherwise be considered optimal.

Indeed, users can apply excess pressure to nasal mask 8, 68 or 88 when self-fitting even if less pressure would suffice (and be optimal) for various reasons, including lack of familiarity with such ventilation interfaces or simple fear of leakage. For instance, fear of leakage may lead a user to take measures that may sacrifice comfort for illusory security.

Inner membrane 3 or 43 can be outwardly curved so that it may begin to curve back on itself. In at least one exemplary embodiment, only a portion of inner membrane 3 or 43 can be curved so as to begin to curve back on itself. Nevertheless, in another exemplary embodiment, inner membrane 3 or 43 can be outwardly curved so that it may curve back on itself substantially. Further, in at least one exemplary embodiment, inner membrane 3, 43 can be curved back into a full loop 53 in cross-section and can be a hollow tubular structure in whole, as shown in FIG. 4. Alternatively, inner membrane 3, 43 or 53 can be a solid tubular structure lacking a channel defined through the center. In such embodiments, the solid construction can provide additional stopper functionality as opposed to an air pocket.

Comparing cushion 10, 40 and 50 FIGS. 2-4, outer sealing membrane 2, 42 or 52 can extend from frame 1, 41 or 51 in a variety of ways. For example, outer sealing membrane need not have a substantial outward protrusion upon extending from frame 1, 41 or 51. Also, inner membrane 3, 43 or 53 can protrude inwardly before being oriented outwardly. Numerous other configurations will be readily recognized by one having ordinary skill in the art having the benefit of this disclosure.

In another exemplary embodiment in reference to full masks as shown in FIG. 5, particularly full masks 68 having a general triangular portion adapted to mate (with or without additional mounting components) with a face cushion 60 having a substantially triangular-shaped frame 61. The face cushion can be a double-membrane cushion 60 having an outwardly oriented inner membrane.

In yet another exemplary embodiment in reference to oral masks or portions of hybrid masks 88 (i.e. those masks having an oral cavity and either nasal inserts or nasal prongs) as shown in FIG. 6 having a general oval portion 93 adapted to mate (with or without additional mounting components) with a face cushion 90 having a substantially oval frame 81. The oral cushion can be a double-membrane cushion 90 having an outwardly oriented inner membrane.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A ventilation interface comprising:
   a cushion;
   the cushion including:
      a central passageway;
      a frame having an upper portion with an inner surface and an outer surface, wherein the span from the inner surface to the outer surface defines a first direction;

an outer sealing membrane; and an inner membrane, wherein the outer sealing membrane has a first terminating end that extends towards the central passageway, wherein the inner membrane has a second terminating end that extends away from the central passageway wherein at least one of the outer sealing membrane and the inner membrane extends from the upper portion of the frame, and the second terminating end of the inner membrane extends beyond the outer surface of the upper portion of the frame in the first direction.

2. The ventilation interface of claim 1, wherein the outer sealing membrane and the inner membrane are integral.

3. The ventilation interface of claim 1, wherein the outer sealing membrane and the inner membrane are separate.

4. The ventilation interface of claim 1, wherein one of the outer sealing membrane and the inner membrane is made of a flexible material.

5. The ventilation interface of claim 1, wherein the inner membrane consists of gel.

6. The ventilation interface of claim 1, wherein the inner membrane consists of foam.

7. The ventilation interface of claim 1, wherein the inner membrane has at least one notch.

8. The ventilation interface of claim 1, wherein the inner membrane curves in a different direction than the outer sealing membrane.

9. The ventilation interface of claim 1, wherein the inner membrane and the outer sealing member are configured to maintain a distance during use.

10. The ventilation interface of claim 1, wherein the outer sealing membrane has a lower portion that extends away from the central passageway.

11. The ventilation interface of claim 1, wherein the inner membrane is configured to trap gas during use.

12. The ventilation interface of claim 1, wherein the outer sealing membrane has a first thickness and the inner membrane has a second thickness; and wherein the second thickness of the inner membrane is greater than the first thickness of the outer sealing membrane.

13. A cushion comprising:
a central passageway;
a frame having an upper portion with an inner surface and an outer surface, wherein the span from the inner surface to the outer surface defines a first direction;
an outer sealing membrane; and
an inner membrane, wherein the outer sealing membrane has a first terminating end that extends towards the central passageway, wherein the inner membrane has a second terminating end that extends away from the central passageway wherein the second terminating end of the inner membrane extends beyond the outer surface of the upper portion of the frame in the first direction.

14. The cushion of claim 13, wherein the outer sealing membrane has a first thickness and the inner membrane has a second thickness; and wherein the second thickness of the inner membrane is greater than the first thickness of the outer sealing membrane.

15. The cushion of claim 13, wherein the inner membrane curves in a different direction than the outer sealing membrane.

16. A ventilation interface comprising:
a cushion;
the cushion including:
a central passageway;
a frame with a first upper portion and second upper portion opposite the first upper portion;
an outer sealing membrane, wherein the outer sealing membrane has an outer membrane terminating end that extends towards the central passageway; and
an inner membrane with a first inner membrane terminating end and a second inner membrane terminating end opposite the first inner membrane terminating end,
wherein the first inner membrane terminating end and the second inner membrane terminating extend away from the central passageway;
wherein at least one of the outer sealing membrane and the inner membrane extends from the frame;
wherein the distance between the first upper portion and second upper portion defines a first width;
wherein the distance between first inner membrane terminating end and the second inner membrane terminating end defines a second width;
wherein the second width is greater than the first width.

17. The ventilation interface of claim 16, wherein the first membrane has a first thickness and the second membrane has a second thickness; and
wherein the first thickness and the second thickness are different.

* * * * *